(12) United States Patent
Baudot et al.

(10) Patent No.: US 7,267,775 B2
(45) Date of Patent: Sep. 11, 2007

(54) GAS PROCESSING METHOD USING A FILTERED GLYCOL SOLUTION

(75) Inventors: Arnaud Baudot, Lyons (FR); Nathalie Dupassieux, Lyons (FR); Sophie Montes, Le Bocage (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 403 days.

(21) Appl. No.: 10/901,971

(22) Filed: Jul. 30, 2004

(65) Prior Publication Data

US 2005/0022665 A1 Feb. 3, 2005

(30) Foreign Application Priority Data

Jul. 30, 2003 (FR) .................................. 03 09411

(51) Int. Cl.
*B01D 61/00* (2006.01)
*B01D 61/02* (2006.01)
*B01D 1/44* (2006.01)
*B01D 53/14* (2006.01)
*B01D 47/00* (2006.01)

(52) U.S. Cl. .................. 210/652; 210/651; 95/200; 95/205; 95/206; 203/47

(58) Field of Classification Search ........ 210/650–654, 210/640; 203/57, 58, 49; 202/153, 159; 95/50, 188
See application file for complete search history.

(56) References Cited

U.S. PATENT DOCUMENTS

| | | | | |
|---|---|---|---|---|
| 3,370,636 A | * | 2/1968 | Francis Jr. et al. | 159/16.3 |
| 3,471,370 A | * | 10/1969 | Jubin Jr. | 203/49 |
| 3,651,617 A | * | 3/1972 | Hodgson | 95/188 |
| 5,194,159 A | * | 3/1993 | George et al. | 210/654 |
| 5,269,933 A | * | 12/1993 | Jehle et al. | 210/640 |
| 5,501,776 A | * | 3/1996 | Lermite et al. | 203/18 |
| 5,505,855 A | * | 4/1996 | Haussmann | 210/652 |
| 5,785,859 A | * | 7/1998 | Raehse et al. | 210/651 |
| 5,817,889 A | * | 10/1998 | Pondebat et al. | 568/679 |
| 5,964,923 A | * | 10/1999 | Lokhandwala | 95/50 |
| 6,071,413 A | * | 6/2000 | Dyke | 210/651 |
| 6,789,288 B2 | * | 9/2004 | Wijmans et al. | 15/188 |

OTHER PUBLICATIONS

Database WPI, Section CH Week 200013, Derwent Publications, London, GB; Class H01, AN 2000-146107 and RU 2 121 392 Nov. 10, 1998.

* cited by examiner

*Primary Examiner*—Ana Fortuna
(74) *Attorney, Agent, or Firm*—Antonelli, Terry, Stout & Kraus, LLP.

(57) ABSTRACT

The invention relates to a method and to a plant for processing a gas by means of a glycol solution wherein a feed comprising a gas, a glycol, water and salts is subjected to a first stage (5) of separating the gas from a liquid effluent and said liquid effluent is subjected to a dehydration stage (14) to recover a dehydrated liquid effluent, characterized in that the salts contained in the liquid effluent, dehydrated or not, are eliminated in a membrane separation stage (10) by means of a driving force generated by mechanical pressure difference on either side of a membrane of pore size ranging between 5 and 100 Angstrom. The invention also relates to the use of the method and of the plant for regeneration of a liquid compound of the glycol family used for hydrate formation prevention when using a natural gas.

6 Claims, 3 Drawing Sheets

GAS PROCESSING METHOD USING A
FILTERED GLYCOL SOLUTION

FIELD OF THE INVENTION

The present invention relates to processing of a hydrocarbon feed with an aqueous glycol solution used for hydrate formation prevention when using a gas, notably a natural gas. The method of the present invention is particularly well-suited for regeneration of a liquid compound of the glycol family used during transportation of a natural gas between the production well and a processing plant.

BACKGROUND OF THE INVENTION

Natural gas at the outlet of production wells is often associated with formation water containing dissolved salts such as, for example, sodium chloride, potassium chloride, calcium chloride, sodium bicarbonate. The natural gas is transported from the production site to a processing site by circulation in lines. In cases where the natural gas is water-saturated and at equilibrium with an aqueous phase, depending on the transportation conditions, hydrate plugs leading to production stop may form. To prevent such problems, a hydrate inhibitor such as glycol is injected into the gas-carrying lines. An aqueous solution containing between 60% and 90% by weight of glycol can be used. After transportation, a mixture consisting of formation water and of glycol is recovered, then processed in a glycol regeneration unit in order to reconcentrate the glycol, i.e. to remove the water. The regenerated glycol can again be injected into the natural gas carrying lines.

Glycol distillation systems for separating the glycol from a mixture comprising water and glycol are known to the man skilled in the art. In general, the systems of the prior art allow an aqueous solution containing between 70% and 90% by weight of glycol to be obtained.

However, regeneration of the glycol leads to concentrate the salts initially present in the formation water in the regenerated glycol. The presence of these salts is often the cause of operating problems linked with the accumulation of these salts on certain parts of the regeneration device. The parts of the regeneration device which are the most sensitive to this salt accumulation are often hot elements, for example the reboilers that equip distillation columns. Accumulation of these salts can lead to irreversible deterioration of these hot elements and induce glycol degradation.

There are membrane separation techniques for carrying out separations on glycol-based liquid compositions. The existing membrane separation techniques can be distinguished by the method of operation of these membranes, this method of operation being generally linked with the stresses or with the driving force applied on either side of the membrane interface.

American patent U.S. Pat. No. 5,505,855 describes a method using a reverse osmosis type membrane separation technique. This patent describes a method of cleaning a contaminated and substantially water-free glycol wherein said glycol is heated, pressurized and passed into a reverse osmosis membrane module to recover a cleaned glycol-based permeate and a retentate comprising the pollutants initially present in the contaminated glycol.

American patent U.S. Pat. No. 5,817,889 describes a method using a membrane separation technique wherein the stress applied on either side of the membrane interface is an electric potential gradient, in this case by means of a technique referred to as electrodialysis. More precisely, this patent describes a method of cleaning glycol solutions comprising salts, wherein an amount of water allowing to recover a hydrocarbon-based phase and a glycol and water based phase is added to the glycol solution, these two phases are separated, and the glycol and water based phase is subjected to a salt elimination treatment using an electrodialysis technique allowing separation of the cations and of the anions of these salts.

The glycol cleaning methods of the prior art using membrane separation techniques involve a certain number of drawbacks that can be linked with the type of membranes used or with their method of operation. For example, the reverse osmosis type membrane interfaces have very small pore sizes, typically below 10 Angstrom, which can cause fouling. These membrane types also require a working pressure often above 4 MPa. Similarly, the membranes used by means of an electric potential gradient, electrodialysis type membranes for example, are very sensitive to the nature of the feed to be treated in terms of selectivity and of fouling. Furthermore, this type of membrane is quite fragile and can readily undergo physical deterioration if the feed contains particles of abrasive nature. Besides, most of the membranes of the prior art are not suited for processing high feed flow rates.

The present invention proposes a method of regenerating an aqueous glycol solution allowing to remove the salts and part of the water while overcoming or limiting the aforementioned drawbacks.

SUMMARY OF THE INVENTION

In general terms, the invention relates to a method of processing a hydrocarbon feed with an aqueous glycol solution, said feed comprising a gas phase, water and dissolved salts. According to the invention, at least part of a liquid effluent comprising glycol, water and salts is dehydrated, and at least part of the liquid effluent is filtered through a membrane so as to separate part of the salts, the membrane having a pore size ranging between 5 and 100 Angstrom, a pressure difference being applied between the two faces of the membrane.

This method is particularly well-suited to the use of a gas, for example for transportation of a natural gas, wherein a liquid compound of the glycol family is used for hydrate formation prevention.

In this definition of the invention, what is referred to as glycol is a compound selected from the group consisting of ethylene glycol, diethylene glycol, triethylene glycol and tetraethylene glycol.

What is understood to be salts is generally sulfates, carbonates, alkaline-earth chlorides and alkaline metals. These salts dissolved in the feed can for example comprise sodium, potassium, magnesium, iron, chlorine, sulfate, carbonate ions.

According to an aspect of the invention, the membrane separation stage is carried out by means of a driving force generated by a pressure difference. The pressure difference applied on either side of the membrane interface can range between 0.5 and 5 MPa, preferably between 0.5 and 4 MPa, more preferably between 0.5 and 3.5 MPa, in particular between 1 and 3 MPa, for example between 1 and 2.5 MPa.

One of the advantages afforded by using a pressure difference membrane separation technique is to take advantage of the pressure at which the feed is available. In relation to the other membrane separation methods used in the prior art, such as reverse osmosis and electrodialysis, the membrane separation of the method according to the invention uses as the driving force inducing material transfer through the membrane only a pressure difference generally less than or equal to 4 MPa, which makes it a less energy-consuming technique than the membrane technologies of the prior art. Reverse osmosis generally requires a concentration difference and a very great pressure difference, generally greater than 4 MPa and most often close to 8 MPa, this great pressure difference being necessary to induce mass transfer through the membrane in the opposite direction to the osmotic flow, i.e. between a concentrated phase, the retentate, and a diluted phase, the permeate. Electrodialysis requires additional energy in form of electric potential differences.

According to another aspect of the invention, the membranes have a pore size ranging between 5 and 100 Angstrom, preferably between 8 and 80 Angstrom, more preferably between 8 and 50 Angstrom, for example between 8 and 30 Angstrom.

According to the invention, the liquid effluent can be expanded prior to being filtered, then dehydrated. The water content of this liquid effluent can be above 10% by weight, most often above 20% by weight, for example 50% by weight.

Alternatively, filtration can be carried out after dehydration of the liquid effluent.

The liquid effluent, dehydrated or not, which is filtered can also comprise hydrocarbons and amines intended to limit corrosion, for example methyl diethanolamine MDEA. The hydrocarbon content and the amine content are generally below 5% by weight.

The feed rate of the liquid effluent, dehydrated or not, that is filtered can range between 1 and 100 m$^3$/h, preferably between 10 and 50 m$^3$/h.

The membrane separation techniques for which the driving force applied on either side of the membrane interface is induced by a pressure gradient are conventionally classified according to a criterion known as cut-off threshold. The cut-off threshold generally corresponds to the minimum size that a molecule in solution must have to be held back upstream from the filter membrane. The membrane separation techniques are generally listed according to their cut-off thresholds. The following can be distinguished, in decreasing cut-off threshold order: microfiltration, ultrafiltration, nanofiltration and reverse osmosis.

Preferably, filtration according to the present invention is carried out by nanofiltration. In terms of cut-off threshold, nanofiltration comes between ultrafiltration and reverse osmosis. Ultrafiltration generally uses membranes permeable to water, salts and ions in solution, and to small molecules of size generally below 5000 g/mol. Reverse osmosis uses only water-permeable membranes. The nanofiltration membranes can have cut-off thresholds ranging between 50 and 5000 g/mol.

Nanofiltration can be distinguished from the other membrane filtration techniques by its permeability and its selectivity. For anionically or cationically charged nanofiltration membranes, i.e. containing for example groups such as, for example, the chemical elements COO$^-$SO3$^-$, the cut-off threshold for the ionized molecules can be below 50 g/mol.

The hydrophilic or hydrophobic properties of the nanofiltration membranes can modify the separation parameters, notably for the feeds to be treated that contain polar solvents.

The definition of the cut-off threshold centred on the size of the molecules to be separated may not be sufficient to define the properties of the nanofiltration membranes, the hydrophilic or hydrophobic properties and the surface charge and pore properties can also be taken into account. The physico-chemical interactions between the membrane and the solute to be treated defined by the size of the molecules, the charges and the polarities, thus condition the specific performances of nanofiltration.

The nanofiltration membranes that can be used in the method according to the invention can correspond to those currently used for separation of low molecular weight oligomer or polymer organic molecules, separation of electrolytes, non-electrolytes, separation of monovalent ions, divalent ions in aqueous solution, for water desalting.

The membranes that can be used in the method according to the invention can comprise a selective polymer layer. By way of example, the selective polymer layer can essentially consist of:

sulfonated polysulfone, such as the membranes manufactured by Nitto-Denko, polyamide, such as the membranes manufactured by Dow, polypiperazineamide, such as the membranes manufactured by Dow or Nitto-Denko, or cellulose acetate, such as the membranes manufactured by Hoechst.

The membranes that can be used in the method according to the invention can also comprise a selective layer of mineral nature, for example essentially consisting of alumina, such as the membranes manufactured by Exekia.

According to a preferred embodiment of the method according to the invention, filtration is carried out by means of a salt-permeable and glycol-impermeable membrane. Alternatively, filtration can be carried out by means of a glycol-permeable and salt-impermeable membrane.

Filtration leads to a stream essentially comprising salts and water, and to a stream essentially comprising glycols and water. In one case, the stream essentially comprising salts and water can constitute the permeate and the stream essentially comprising glycol and water can constitute the retentate. In another case, the stream essentially comprising salts and water can constitute the retentate and the stream essentially comprising glycol and water can constitute the permeate.

In the case where the stream essentially comprising glycol and water constitutes the permeate, the membrane NF70 manufactured by Dow/Filmtec, which has a high rejection rate for organic compounds whose size is close to monoethylene glycol (MEG), can be used.

According to the invention, the feed can be mixed with the aqueous glycol solution, then the mixture can be transported by circulation in a line, and the gas phase is thereafter separated from the liquid effluent.

The natural gas separation stage is often a gas/liquid type separation during which the natural gas is collected on the one hand and a liquid effluent is collected on the other. Thus, this liquid effluent is often available at a high pressure generally ranging between 3 and 15 MPa.

The method can advantageously comprise an expansion stage before the membrane separation stage, wherein the liquid feed can be expanded to a pressure ranging between 0.5 and 5 MPa, preferably between 0.5 and 4 MPa, more preferably between 0.5 and 3.5 MPa, in particular between 1 and 3 MPa, for example between 1 and 2.5 MPa.

Thus, in the method of the invention, it is not necessary to add a pumping and pressurization system upstream from the membrane, as it is generally the case in all the other types of industrial nanofiltration applications. The method according to the invention thus allows to limit the operating and maintenance costs.

The dehydration stage is applied to the liquid effluent from the natural gas separation stage or to the feed essentially comprising glycol and water from the membrane separation stage. This dehydration stage can be carried out by distillation at atmospheric pressure.

The residue from the dehydration stage using atmospheric distillation mainly comprises glycol compounds and water traces. The liquid effluent obtained after filtration can be recycled, for example re-injected into the top of the well.

The object of the invention is also a plant for processing a hydrocarbon feed with an aqueous glycol solution, said feed comprising a gas phase, water and dissolved salts. The plant comprises means for regenerating a liquid effluent comprising glycol and salts, said regeneration means comprising a dehydration device and a membrane separation system comprising at least one membrane of pore size ranging between 5 and 100 Angstrom, suited to eliminate part of the salts contained in the effluent.

According to the invention, the membrane separation system can comprise means intended for tangential circulation of the liquid effluent in relation to the membrane.

Preferably, the membrane separation system comprises a module consisting of several membranes arranged in a housing. More preferably, the membrane separation system can comprise several membrane modules arranged in series and/or in parallel.

BRIEF DESCRIPTION OF THE FIGURES

For better understanding, an embodiment of the method according to the invention is illustrated in FIG. 1.

DETAILED DESCRIPTION

Figure 1:
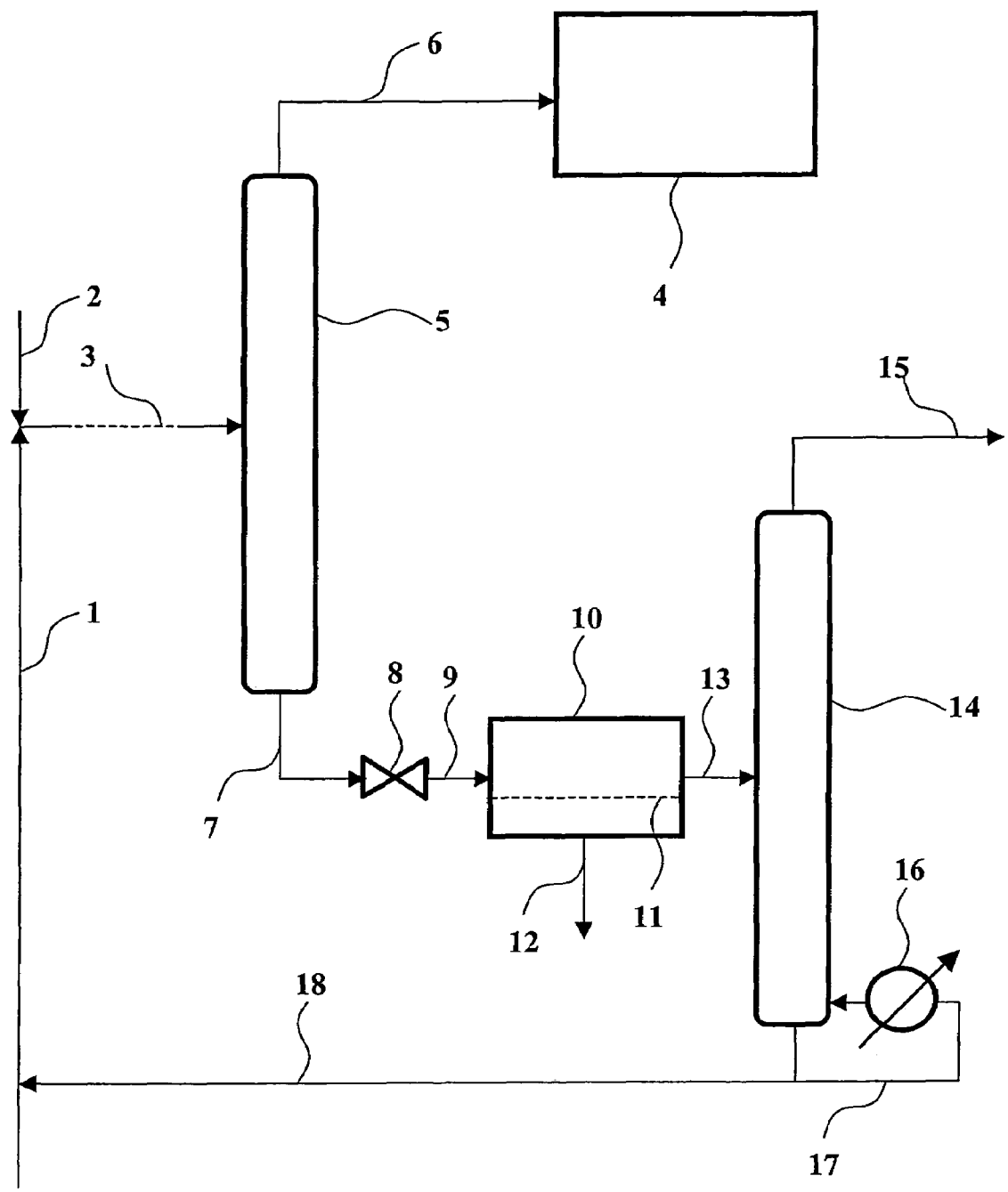

Glycol containing 20% to 40% water is injected, at the top of the well, by means of a supply line 1, to be mixed with the natural gas delivered through a line 2 at a pressure of approximately 8 MPa. Glycol injection thus allows to prevent hydrate formation as the natural gas flows through a carrying line 3 to a gas processing plant 4. The natural gas is then separated from the glycol in a gas/liquid separator 5. The natural gas is recovered at the top of the separator by means of a line 6 through which it is discharged towards gas processing plant 4. The glycol containing about 60% water is recovered at a pressure of the order of 8 MPa in a line 7. This pressure approximately corresponds to the flowing pressure in line 3 upstream from the gas/liquid separation stage. The glycol is then sent through an expander 8 to be expanded to a pressure of 2 MPa. The glycol thus expanded is sent through a line 9 to an assembly 10 comprising nanofiltration membrane modules. A fraction of the water contained in the glycol and a fraction of the associated dissolved salts are extracted from the glycol stream by permeation through a membrane diagrammatically shown by reference number 11. The water fraction and the salts are discharged through line 12. The glycol is recovered in a line 13 prior to being sent to separation means, a distillation column 14 in the present case, allowing to separate the glycol from the water. The water is discharged through a line 15 at the top of the column. Column 14 is equipped at the base thereof with a reboiler 16 arranged on a recycling line 17 and with a glycol discharge line 18. The glycol is re-injected into the top of the well by means of said line 18.

The membrane surface is so selected that the salt concentration in the glycol solution after the membrane separation stage is lower than the saturation threshold of the solution at the temperature of the reboiler of the dehydration stage.

The nanofiltration stage affords two additional advantages:

it constitutes a purge allowing to selectively remove the salts from the glycol stream and to maintain their concentrations below the saturation threshold at any point of the circuit, and it allows to carry out separation of a large portion of the water recovered during the first separation stage prior to the second separation stage.

Figure 2:
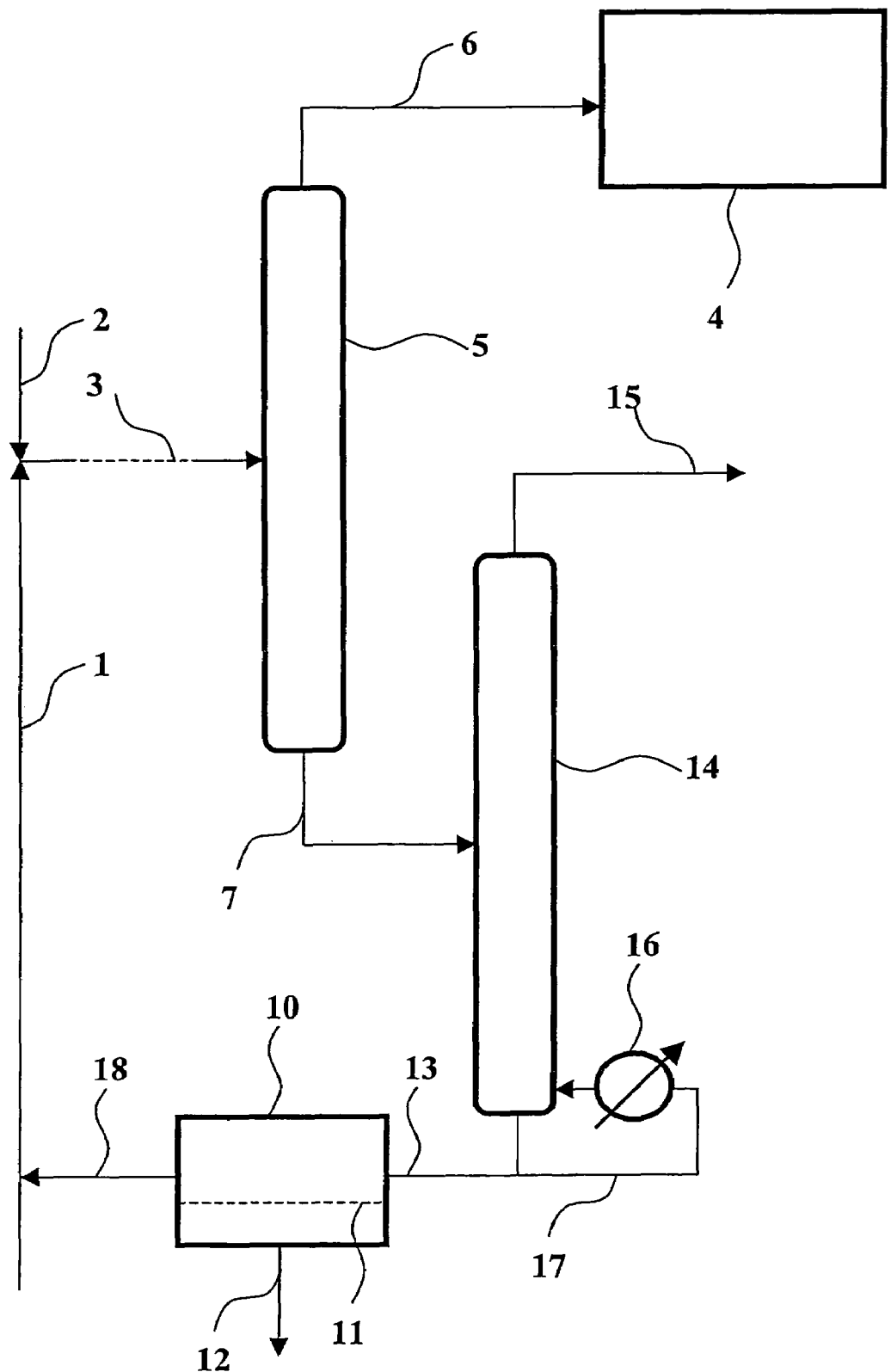
FIGS. 2 and 3 show variants of the method according to the invention. These embodiments are given by way of non-limitative example. These illustrations of the method of the invention do not include all of the components required to implement it. Only the elements necessary for understanding of the invention are shown, and the man skilled in the art will be able to complete these representations to implement the invention.
Figure 3:
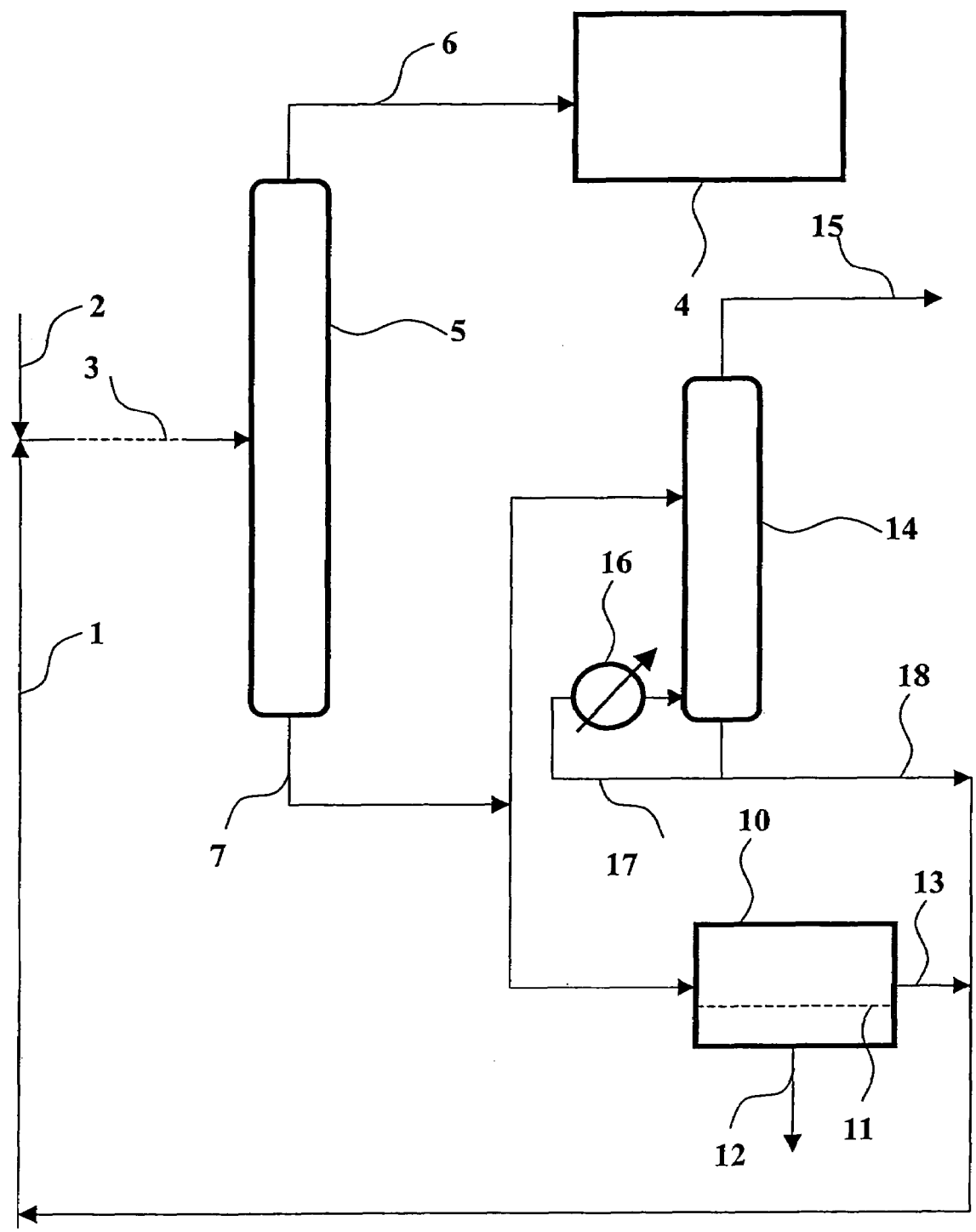

The reference numbers of FIGS. 2 and 3 identical to the reference numbers of FIG. 1 designate the same elements. In FIGS. 2 and 3, the order of the dehydration and filtration stages respectively carried out in distillation column 14 and in assembly 10 is modified.

In FIG. 2, the glycol recovered in line 7 at the bottom of the separator 5 is sent to distillation column 14. Prior to being fed into column 14, the glycol can be expanded. The water and possibly hydrocarbons are discharged through line 15 at the top of column 14. The glycol discharged through line 13 at the bottom of column 14 is fed into assembly 10 comprising nanofiltration membrane modules. Prior to being fed into assembly 10, the glycol can be compressed. The glycol recovered through discharge line 18 at the outlet of assembly 10 is re-injected into the top of the well by means of line 1.

Distillation in column 14 has the advantage of freeing the glycol from possible hydrocarbons absorbed during transportation in line 3. Thus, membrane 11 is not polluted or deteriorated by the presence of hydrocarbons in the glycol to be filtered.

In FIG. 3, the glycol recovered in line 7 is separated into two streams. Part of the glycol is possibly expanded, then fed into distillation column 14. Another part is possibly expanded, then fed into assembly 10 comprising nanofiltration membrane modules. The glycol recovered through discharge line 18 at the bottom of column 14 and the glycol recovered through line 13 at the outlet of assembly 10 are possibly compressed, then re-injected into the top of the well by means of line 1.

Without departing from the scope of the invention, combinations between the various embodiments described in connection with FIGS. 1, 2 and 3 are possible.

The invention claimed is:

1. A method of processing a hydrocarbon feed with an aqueous glycol solution, said feed comprising a gas phase, water and dissolved salts, wherein the gas is separated from a liquid effluent, at least part of the liquid effluent comprising glycol, water and salts is dehydrated, and at least part of the liquid effluent containing glycol and salt is filtered by nanofiltration through a membrane so as to separate part of the salts, the membrane having a pore size ranging between 5 and 100 Angstrom, a pressure difference being applied between the two faces of the membrane.

2. A method as claimed in claim 1, wherein the liquid effluent is expanded prior to being filtered, then dehydrated.

3. A method as claimed in claim 1, wherein the filtered liquid effluent is recycled.

4. A method as claimed in claim 1, wherein the pressure difference ranges between 0.5 and 5 MPa.

5. A method as claimed in claim 1, wherein the membrane is salt-permeable and glycol-impermeable.

6. A method as claimed in claim 1, wherein the feed is a natural gas at a pressure above 0.5 MPa.

* * * * *